(12) United States Patent
Wang et al.

(10) Patent No.: US 11,390,700 B2
(45) Date of Patent: Jul. 19, 2022

(54) PROPYLENE-ETHYLENE RANDOM COPOLYMER WITH IMPROVED IRRADIATION RESISTANCE

(71) Applicant: Borealis AG, Vienna (AT)

(72) Inventors: Jingbo Wang, Linz (AT); Markus Gahleitner, Linz (AT); Andreas Albrecht, Linz (AT); Satu Rintakari, Karhunkyla (FI); Friedrich Berger, Linz (AT); Martina Sandholzer, Linz (AT)

(73) Assignee: BOREALIS AG, Vienna (AT)

( * ) Notice: Subject to any disclaimer, the term of this patent is extended or adjusted under 35 U.S.C. 154(b) by 485 days.

(21) Appl. No.: 16/494,627

(22) PCT Filed: May 16, 2018

(86) PCT No.: PCT/EP2018/062643
§ 371 (c)(1),
(2) Date: Sep. 16, 2019

(87) PCT Pub. No.: WO2018/210893
PCT Pub. Date: Nov. 22, 2018

(65) Prior Publication Data
US 2020/0129649 A1 Apr. 30, 2020

(30) Foreign Application Priority Data
May 18, 2017 (EP) ..................................... 17171704

(51) Int. Cl.
*C08F 210/06* (2006.01)
*C08F 210/16* (2006.01)
(Continued)

(52) U.S. Cl.
CPC .......... *C08F 210/06* (2013.01); *C08F 4/6492* (2013.01); *C08F 4/6546* (2013.01);
(Continued)

(58) Field of Classification Search
CPC .... C08F 210/06; C08F 4/6492; C08F 4/6546; C08F 210/16; C08F 2500/12; C09D 123/14; C09D 123/16; A61L 2/081
See application file for complete search history.

(56) References Cited

U.S. PATENT DOCUMENTS 4,888,369 A 12/1989 Moore
5,234,879 A 8/1993 Garoff et al.
(Continued)

FOREIGN PATENT DOCUMENTS

CN 105934475 A 9/2016
EP 586390 A1 3/1994
(Continued)

OTHER PUBLICATIONS

Gahleitner, et al. "Sterilization Effects on Polypropylene: Technology and Polymer Type Effects", OFI—Institute for Medical Products, Proc. 9th, European Place Conference, 2003 Rome.
(Continued)

*Primary Examiner* — Ali Z Fadhel
(74) *Attorney, Agent, or Firm* — Lowenstein Sandler LLP

(57) ABSTRACT

The present invention deals with a new unimodal propylene-ethylene random copolymer providing improved resistance against gamma irradiation as well as compositions comprising the new unimodal propylene-ethylene random copolymer and final articles made therefrom.

18 Claims, 1 Drawing Sheet

(51) Int. Cl.
*C09D 123/14* (2006.01)
*C09D 123/16* (2006.01)
*C08F 4/649* (2006.01)
*C08F 4/654* (2006.01)
*A61L 2/08* (2006.01)

(52) U.S. Cl.
CPC .......... *C08F 210/16* (2013.01); *C09D 123/14* (2013.01); *C09D 123/16* (2013.01); *A61L 2/081* (2013.01); *C08F 2500/12* (2013.01)

(56) References Cited

U.S. PATENT DOCUMENTS

| | | | |
|---|---|---|---|
| 6,300,420 B1* | 10/2001 | Jaaskelainen | C08L 23/142 525/240 |
| 7,452,953 B2* | 11/2008 | Jaaskelainen | C08F 297/083 526/348 |
| 2004/0175591 A1 | 9/2004 | Jaaskelainen | C08F 210/16 428/515 |
| 2004/0210012 A1* | 10/2004 | Jaaskelainen | C08F 297/08 526/348.1 |
| 2013/0212993 A1* | 8/2013 | Tynys | D01D 5/10 428/401 |
| 2014/0357816 A1* | 12/2014 | Virkkunen | C08F 4/50 526/123.1 |
| 2015/0218355 A1* | 8/2015 | Hemmeter | C08L 51/06 521/91 |
| 2015/0274907 A1* | 10/2015 | MacDonald | C08L 23/12 526/348 |

FOREIGN PATENT DOCUMENTS

| | | |
|---|---|---|
| EP | 591224 A1 | 4/1994 |
| EP | 0801104 A1 | 10/1997 |
| EP | 2610270 A1 | 7/2013 |
| EP | 2610271 A1 | 7/2013 |
| EP | 2610272 A1 | 7/2013 |
| EP | 491566 | 1/2017 |
| EP | 3115412 A1 | 1/2017 |
| WO | 9219653 A1 | 11/1992 |
| WO | 9219658 A1 | 11/1992 |
| WO | 9933843 A1 | 7/1999 |
| WO | 2009/027389 A1 | 3/2009 |
| WO | 2010078479 A1 | 7/2010 |
| WO | 2012007430 A1 | 1/2012 |
| WO | 2105/117948 A1 | 8/2015 |
| WO | 2015117948 A1 | 8/2015 |

OTHER PUBLICATIONS

Singh, et al., "Triad Sequence Determination of Ethylene-Propylene Copolymers—Application of Quantitative 13C NMR," Polymer Testing, 2009, vol. 29, pp. 475-479.

Zhou, et al., "A new decoupling method for accurate quantification of polyethylene copolymer composition and triad sequence distribution with 13C NMR," Journal of Magnetic Resonance, vol. 187, 2007, pp. 225-233.

Busico, et al., "Alk-1-ene Polymerization in the Presence of a Monocyclopentadienyl Zirconium (iv) Acetamidinate Catalyst: Microstructural and Mechanistic Insights a," Macromolecular Rapid Commun., vol. 28, 2007, pp. 1128-1134.

Cheng, H.N., "C NMR Analysis of Ethylene-Propylene Rubbers," Macromolecules, 1984, vol. 17, pp. 1950-1955.

Wang, et al., "Structural Analysis of Ethylene/Propylene Copolymers Synthesized with a Constrained Geometry Catalyst," Macromolecules, 2000, vol. 33, pp. 1157-1162.

Koenig, "Theory of Polymer Characterization" Spectroscopy of Polymers, Lack, American Chemical Society, Washington, DC 1992, p. 9.

Ortin, A. et al., "Development of an Automated Cross-Fractionation Apparatus (TREF-GPC)for a Full Characterization of the Biuvariate Distribution of Polyolefins", Macromol. Symp. 2007, 257, pp. 13-28.

Fromme H., et a. "Occurrence of Phthalates and Bisphenol A and F in the Environment", Water Rearch 36 (2002) pp. 1429-1438.

K. Joen et al. "Maximum Rate of Crystallization and Morphology of Random Propylene Ethylene Copolymers as a Function of omonomer Content up to 21 mol%", Marcolecules, vol. 41, No. 1, Jan. 1, 2008, pp. 95-108.

Written Opinion of the International Preliminary Examining Authority for PCT/EP2018/062643 dated Apr. 12, 2019, 5 pages.

Notification of Transmittal of the International Preliminary Report on Patentability for PCT/EP2018/062643 dated Aug. 14, 2019, 13 pages.

Notification of Transmittal of the International Search Report and the Written Opinion of the International Searching Authority, or the Declaration for Application No. PCT/EP2018/062643 dated Aug. 1, 2018 14 pages.

* cited by examiner

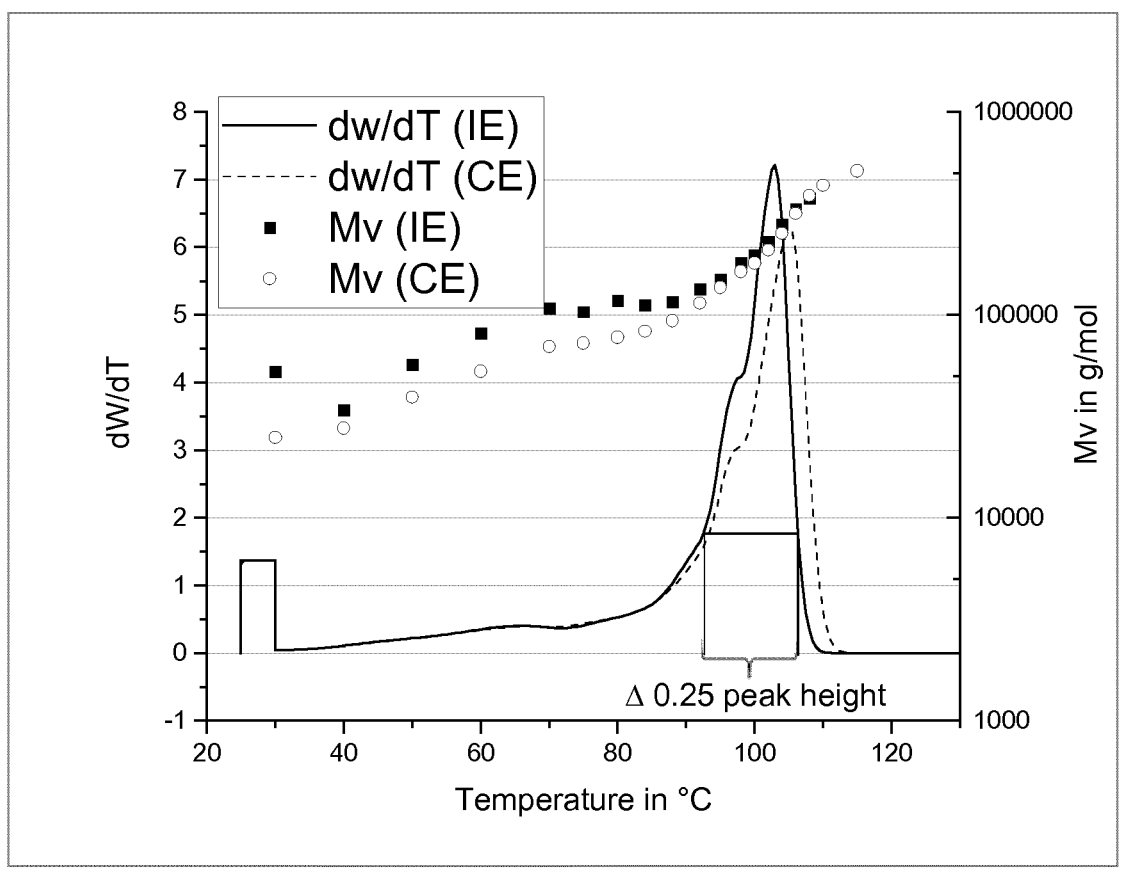

PROPYLENE-ETHYLENE RANDOM COPOLYMER WITH IMPROVED IRRADIATION RESISTANCE

CROSS-REFERENCE TO RELATED APPLICATION(S)

This application is a national phase of International Application No. PCT/EP2018/062643, filed on May 16, 2018, which claims the benefit of European Patent Application No. 17171704.4, filed on May 18, 2017. The contents of these applications are hereby incorporated by reference in their entirety.

TECHNICAL FIELD

The present invention deals with a new unimodal propylene-ethylene random copolymer providing improved resistance against gamma irradiation as well as compositions comprising the new unimodal propylene-ethylene random copolymer and final articles made therefrom.

BACKGROUND INFORMATION

Polypropylene (PP) is one of the most used plastics for packaging applications. In a continuously increasing part of this market, the material is sterilized in either heat (steam), radiation (β/electrons or γ) or chemicals (mostly ethylene oxide), which affects the mechanical and optical properties.

Among all these, the sterilization via γ-radiation is the most relevant method for sterilizing pharmaceutical, medical or diagnostic items.

It is well known, that radiation, mostly the effect of γ-rays, induce chain scission and degradation effects, resulting in a reduced melt viscosity and severe embrittlement. What makes this radical reaction so critical is the fact that it continues for long times after the actual sterilization process, making long-term studies necessary for studying the effects.

DESCRIPTION OF THE PRIOR ART

Various strategies have been published for a reduction of these effects:

Some focus on the use of "mobilizing agents" (paraffinic oils) and special stabilizer formulations. Others combine the polypropylene with specific polyethylene qualities or other polymers: U.S. Pat. No. 4,888,369 discloses a high energy radiation resistant polypropylene composition. It consists essentially of substantially crystalline normally solid polypropylene having a narrow molecular weight distribution, and, dispersed therein at a concentration effective to increase substantially the high energy radiation resistance of the polypropylene, a synergistic mixture of: (1) a hindered amine component, (2) a hindered phenolic component, and (3) a phosphorous containing component, the weight ratios of component (1) to component (2) to component (3) being about 1:(0.1-2):(0.1-2). Also disclosed are radiation sterilized articles in which at least part of the material of construction comprises the polypropylene composition.

EP0801104 discloses the use of an amorphous polypropylene consisting of a homopolymer of propylene or a copolymer of propylene with one or more alpha-olefins with a propylene content of at least 80 mol.-%, having a melt enthalpy of at most 40 J/g and a melt flow index of 0.1-100 g/10 min, as additive to improve the stability to ionizing radiation. The addition of amorphous material leads to high migration levels due to oligomers present in the amorphous material.

Sterilization effects on polypropylene (Markus Gahleitner, et. al. Proc. 9th European PLACE Conference (2003) Rome), describes changes in mechanical properties of various polypropylene homopolymers and random copolymers after irradiation at 50 kGy. These results give an indication of the mechanical properties for short periods after sterilization. However, these results do not give any indication on the long term behaviour of irradiated polymer samples.

There is a constant need within the Health Care industry to have polymers at hand, which can be used for medical articles, withstand higher dosages of irradiation and retain the mechanical properties, like impact behaviour at a higher level and for a longer time after irradiation had taken place.

So the present inventors have sought new propylene-random copolymers, developed in particular for the health care and medical market, which possess improved resistance for γ-irradiation. This improvement should not be at the expense of any other properties of the polymer or any article formed. Thus, other mechanical properties, e.g. stiffness or low levels of fractions soluble in cold xylene (XCS), should be maintained.

OBJECT OF THE INVENTION

It has been an objective for the present invention to provide a unimodal polypropylene random copolymer as well as a polypropylene random copolymer compositions comprising the unimodal propylene-ethylene random copolymer which show improved long term retention of mechanical properties after irradiation, especially improved long term retention of impact strength after irradiation.

The present inventors have sought for possibilities to modify the polymer structure of propylene-ethylene random copolymers in such a way, that the polymers provide improved long term retention of impact strength after irradiation.

Seen from another point of view, the present inventors have sought for possibilities to provide propylene-ethylene random copolymers with a specific comonomer distribution.

So the present inventors have surprisingly identified a unimodal random copolymer of propylene and 2.0-4.5 wt.-% of ethylene characterised by a specific incorporation of the ethylene comonomer.

In particular the present inventors have identified a unimodal polypropylene random copolymer of propylene and 2.0-4.5 wt.-% of ethylene as comonomer characterised by a comonomer distribution (CD) determined via a-TREF of at most 16.0[−].

In a further embodiment, the invention encompasses a polypropylene random copolymer composition comprising a unimodal polypropylene random copolymer of propylene and 2.0-4.5 wt.-% of ethylene as comonomer wherein the latter is characterised by a comonomer distribution (CD) determined via a-TREF of at most 16.0 [−].

In still a further alternative embodiment the invention relates to moulded articles comprising the unimodal polypropylene random copolymer or the polypropylene random copolymer composition as described herein.

In still a further alternative embodiment the invention relates to the use of the unimodal propylene-ethylene random copolymer of the present invention or the polypropylene random copolymer composition of the present invention or any articles produced thereof for gamma-irradiation applications.

In another alternative embodiment of the present invention, the unimodal random copolymer of propylene and 2.0-4.5 wt.-% of ethylene has been polymerized in the presence of a) a Ziegler-Natta catalyst (ZN-C) comprising compounds (TC) of a transition metal of Group 4 to 6 of IUPAC, a Group 2 metal compound (MC) and an internal donor (ID), wherein said internal donor (ID) is preferably a non-phthalic compound, more preferably a non-phthalic acid ester; b) optionally a co-catalyst (Co), and c) optionally an external donor (ED). It is most preferred that the internal donor (ID) is selected from optionally substituted malonates, maleates, succinates, glutarates, cyclohexene-1,2-dicarboxylates, benzoates and any derivatives and/or mixtures thereof, preferably the internal donor (ID) is selected from e.g. substituted maleates and citraconates, most preferably from citraconates; and that the molar ratio of co-catalyst (Co) to external donor (ED) [Co/ED] is 5 to 45.

BRIEF DESCRIPTION OF THE DRAWINGS

FIG. 1 depicts a Cross Fractionation Chromatography (CFC) contour plot from a-TREF-curve.

DETAILED DESCRIPTION

Within this application the terms "unimodal polypropylene random copolymer of propylene and 2.0-4.5 wt.-% of ethylene as comonomer" and "unimodal propylene-ethylene random copolymer" as well as "unimodal polypropylene random copolymer" are understood as synonyms and can be used interchangeable.

Unimodal Propylene-Ethylene Random Copolymer

The unimodal propylene-ethylene random copolymer of the present invention has a comonomer content in a very specific range. Thus the ethylene comonomer content of the unimodal propylene-ethylene random copolymer is in the range of 2.0 to 4.5 wt.-%, preferably in the range of 2.5 to 4.2 wt.-% and more preferably in the range of 3.0 to 3.9 wt.-%.

The unimodal random copolymer of propylene and 2.0-4.5 wt.-% of ethylene may have a melt flow rate $MFR_2$ (230° C.) measured according to ISO 1133 of in the range of 1.0-30.0 g/10 min, preferably in the range of 5.0 to 28.0 g/10 min, like the range of 10.0 to 25.0 g/10 min or 15.0-22.0 g/10 min.

The unimodal random copolymer of propylene and 2.0-4.5 wt.-% of ethylene usually comprises low amounts of fractions soluble in cold xylene (XCS). The amount of XCS may be up to 10.0 wt.-%, preferably up to 9.5 wt.-% or more preferably up to 9.0 wt.-%.

The amount of XCS in the unimodal propylene-ethylene random copolymer can also be at least 3.0 wt.-%, alternatively in the range of 3.0-10.0 wt.-%, like 4.0-9.5 wt.-% or 5.0-9.0 wt.-%.

Comonomer Distribution:

Without being bound to any theory, the present inventors believe, that way of incorporation of the comonomer into the polymer chain has significant influence on the radiation resistance of a polymer: Chain scission seems to occur predominantly in segments with long sequences of propylene monomers. On the other hand's side, polymer segments with regular interruption of such long sequences by comonomers incorporated regularly therein are less prone to chain scission and accordingly more resistant to γ-irradiation.

Such polymers with regular incorporation of comonomers can be classified as having a high randomness.

The randomness of a polymer can be determined either by evaluation the Cross Fractionation Chromatography contour plot produced via a-TREF or via NMR:

When characterised via Cross Fractionation Chromatography (a-TREF×SEC), the randomness can be characterized by the broadness of comonomer distribution (CD, as described in the methods section), wherein a narrow comonomer distribution reflects a high randomness.

The unimodal random propylene-ethylene copolymer of the present invention is characterised by narrow comonomer distribution of at most 16.0 [–] or below, such as at most 15.5 [–] or lower, like at most 14.5 [–] or 13.5 [–] or 13.0 [–] or lower when determined via CFC and a-TREF.

Given the comonomer distribution is determined as a ratio, it is noted to be unitless and accordingly indicated with "[–]".

Koenig B Parameter

The unimodal random propylene-ethylene copolymer of the present invention is characterised by a specific randomness, defined by a Koenig B value of at least 0.8 [–] or higher, preferably in the range of 0.8-0.9 [–]; like 0.80-0.87 [–], preferably in the range of 0.81-0.85 [–].

Given the Koenig B parameter represents a ratio, it is noted to be unitless and accordingly indicated with "[–]".

Molecular Weight and Molecular Weight Distribution:

The unimodal random propylene-ethylene copolymer of the present invention can be characterised by a molecular weight (Mw) of 255-760 kg/mol, and/or a molecular weight distribution MWD being the ratio of the (Mw/Mn) of 3.5 to 8.0, preferably 4.0 to 7.5.

The unimodal random propylene-ethylene copolymer of the present invention may be produced in the presence of a Ziegler-Natta catalyst, which will be described in detail below.

The unimodal random propylene ethylene copolymer of the present invention can be produced in one single reactor. Such a reactor can be a slurry reactor (SR) or can be any continuous or simple stirred batch tank reactor or loop reactor operating in bulk or slurry. Bulk means a polymerization in a reaction medium that comprises of at least 60% (w/w) monomer. According to the present invention the slurry reactor (SR) is preferably a (bulk) loop reactor (LR).

It is preferred that the propylene-ethylene copolymers are produced in the presence of (a) a Ziegler-Natta catalyst (ZN-C) comprises a titanium compound (TC), a magnesium compound (MC) and an internal donor (ID), wherein said internal donor (ID) is a nonphthalic acid ester, (b) optionally a co-catalyst (Co), and (c) optionally an external donor (ED).

Polypropylene Random Copolymer Composition

A polypropylene random copolymer composition of the present invention comprises the unimodal propylene-ethylene random copolymer as described earlier.

The polypropylene random copolymer composition comprises at least 50 wt.-% of the unimodal propylene-ethylene random copolymer, preferably at least 70 wt.-%, more preferably at least 90 wt.-%, yet more preferably at least 95.0 wt.-% or at least 97.0 wt.-% of the unimodal propylene-ethylene random copolymer of the present invention.

Further Components

The instant polypropylene composition may comprise a polyethylene (PE), preferably a low density polyethylene (LDPE) or a linear low density polyethylene (LLDPE).

The polyethylene may be present in the polypropylene random copolymer composition with up to 50 wt.-%, such as up to 30 wt.-% or below, like up to 10.0 wt.-% or up to 5.0 wt.-%, like up to 3.0 wt.-%.

It is preferred if the polyethylene present in the polypropylene random copolymer composition forms 0.5-10.0 wt.-%, like 1.0-5.0 or 1.5-3.0 wt.-% of the total polypropylene random copolymer composition.

Preferably the polyethylene (PE) has a density measured according to ISO 1183-187 in the range of 905 to 925 kg/m$^3$, more preferably in the range of 910 to 922 kg/m$^3$.

A further characteristic feature of the polyethylene (PE) is its melt flow rate. Accordingly it is appreciated that the polyethylene (PE) has a melt flow rate MFR$_2$ (190° C.) of up to 30 g/10 min, more preferably in the range of 1.0 to 30.0 g/10 min, yet more preferably in the range of 5.0 to 20.0 g/10 min.

In a preferred embodiment the polyethylene (PE), i.e. the low density polyethylene (LDPE), is an ethylene copolymer or an ethylene homopolymer, the latter being preferred.

A low density polyethylene (LDPE) especially suitable can be e.g. CA8200 produced in a high pressure autoclave process having a melt flow rate (190° C./2.16 kg) of 7.5 g/10 min, a melting point (DSC) of 108° C. and a density of 920 kg/m$^3$. CA8200 is commercially available from *Borealis AG*, Austria.

Mechanical Properties Before Irradiation

The polypropylene random copolymer composition of the present invention is characterised by well balanced stiffness and impact behavior.

The polypropylene random copolymer composition of the present invention may have a Flexural Modulus measured according to ISO 178 of at least 900 MPa or higher, such as 950 MPa or higher.

The polypropylene random copolymer composition of the present invention may have a Charpy notched impact strength measured according to ISO179/1eA+23° C. of at least 5.6 kJ/m$^2$ or higher.

Mechanical Properties after Irradiation

The unimodal propylene-ethylene random copolymer of the present invention and the polypropylene random copolymer compositions comprising the unimodal propylene-ethylene random copolymer are characterised by good retention of the mechanical properties, especially a good retention of the impact behaviour after long time after irradiation.

The person skilled is aware, that the radical reaction induced by irradiation continues for long times after the actual sterilization process had taken place. To simulate and accelerate the long term behaviour, irradiated samples are exposed to elevated temperatures (i.e. 80° C.). The mechanical properties, especially impact behaviour, are tested afterwards.

Retained Notched Impact Strength after Radiation rNIS$_{(rad; days)}$

The unimodal propylene-ethylene random copolymer of the present invention and polypropylene random copolymer composition comprising it are characterised by a good retention of the impact behaviour, in particular by a good Retained Notched Impact Strength after Radiation rNIS$_{(rad; days)}$, wherein "rad" indicates the irradiation dosage in kGy and "days" indicate the consecutive exposure of the irradiated samples in days at 80° C.

Retained Notched Impact Strength (rNIS$_{(rad; days)}$,) is determined according to the formula:

$$rNIS_{(rad;days)}[\%] = \frac{\gamma NIS_{(rad;days)} * 100}{NIS_{(0;days)}} \qquad (\text{Equ. I})$$

wherein:

$\gamma NIS_{(rad; days)}$) denominates notched impact strength of an irradiated and heat aged sample, and NIS$_{(0; days)}$ denominates the notched impact strength of the same, heat-aged but non-irradiated sample.

Again, "rad" indicates the irradiation dosage in kGy and "days" indicate the consecutive exposure of the irradiated samples in days at 80° C.

Both $\gamma NIS_{(rad; days)}$ and NIS$_{(0; days)}$) are determined according to Charpy ISO 179/1eA+23° C.

Retained Notched Impact Strength after Radiation rNIS$_{(rad; days)}$ is determined by putting into relation the ($\gamma NIS_{(rad; days)}$) to the NIS$_{(0; days)}$ of the same, heat-aged but non-irradiated material.

Polypropylene random copolymer composition of the present invention are characterised by a retained notched impact strength rNIS$_{(50, \geq 60)}$ of at least 82.0%, or at least 85%. Preferably, the polypropylene random copolymer compositions of the present invention are characterised by a rNIS$_{(50, \geq 90)}$ of at least 82.0%, or at least 85% or higher.

More preferably, the polypropylene random copolymer compositions of the present invention are characterised by a rNIS$_{(50; \geq 120)}$ of at least 82.0% or higher, such as 85% or higher. The polypropylene random copolymer composition of the present invention can be further characterised by a rNIS$_{(50; \geq 150)}$ of at least 82.0%, or at least 85% or higher, such as at least 90% or at least 95% or higher.

Catalyst System

As pointed out above the catalyst for the preparation of the present polymer as defined may be a Ziegler-Natta catalyst, in particular a high yield Ziegler-Natta catalyst (so called fourth and fifth generation type to differentiate from low yield, so called second generation Ziegler-Natta catalysts), which comprises a catalyst component, a co-catalyst component and an internal donor based on phthalate-compositions.

Examples for such catalysts are in particular disclosed in U.S. Pat. No. 5,234,879, WO92/19653, WO 92/19658 and WO 99/33843.

However, some of such phthalate-compositions are under suspicion of generating negative health and environmental effects and will probably be banned in the future. Furthermore, there is an increasing demand on the market for "phthalate-free polypropylene" suitable for various applications, e.g. in the field of packaging and medical applications as well as personal care, or personal hygiene.

WO 2012007430 is one example of a limited number of patent applications, describing phthalate free catalysts based on citraconate as internal donor.

However, within this invention it is a preferred option, that unimodal propylene-ethylene random copolymer of the present invention and the polypropylene random copolymer composition of the present invention are free of phthalic acid esters as well as decomposition products thereof, i.e. the composition as a whole meets the maximum of 10 μg/kg, i.e. 10 ppb by weight. In other words any further component being within the scope of the claims due to the comprising wording also has to meet the criteria as set forth above.

A possible catalyst for being used in the production of the polypropylene composition is described herein:

The catalyst is a solid Ziegler-Natta catalyst (ZN-C), which comprises compounds (TC) of a transition metal of Group 4 to 6 of IUPAC, like titanium, a Group 2 metal compound (MC), like a magnesium, and an internal donor (ID) being a phthalate or preferably a non-phthalic compound, preferably a non-phthalic acid ester, still more preferably being a diester of non-phthalic dicarboxylic acids as described in more detail below. Thus, the catalyst is in a preferred embodiment fully free of undesired phthalic compounds. Further, the solid catalyst is preferably free of any external support material, like silica or $MgCl_2$, but the catalyst is self-supported.

The Ziegler-Natta catalyst (ZN-C) can be further defined by the way as obtained. Accordingly, the Ziegler-Natta catalyst (ZN-C) is preferably obtained by a process comprising the steps of a)

$a_1$) providing a solution of at least a Group 2 metal alkoxy compound (Ax) being the reaction product of a Group 2 metal compound (MC) and a monohydric alcohol (A) comprising in addition to the hydroxyl moiety at least one ether moiety optionally in an organic liquid reaction medium; or $a_2$) a solution of at least a Group 2 metal alkoxy compound (Ax') being the reaction product of a Group 2 metal compound (MC) and an alcohol mixture of the monohydric alcohol (A) and a monohydric alcohol (B) of formula ROH, optionally in an organic liquid reaction medium; or $a_3$) providing a solution of a mixture of the Group 2 alkoxy compound (Ax) and a Group 2 metal alkoxy compound (Bx) being the reaction product of a Group 2 metal compound (MC) and the monohydric alcohol (B), optionally in an organic liquid reaction medium; or $a_4$) providing a solution of Group 2 alkoxide of formula $M(OR_1)_n(OR_2)_m X_{2-n-m}$ or mixture of Group 2 alkoxides $M(OR_1)_n X_{2-n'}$ and $M(OR_2)_m X_{2-m'}$, where M is Group 2 metal, X is halogen, $R_1$ and $R_2$ are different alkyl groups of $C_2$ to $C_{16}$ carbon atoms, and $0 \leq n < 2$, $0 \leq m < 2$ and $n+m+(2-n-m)=2$, provided that both n and m≠0, $0 < n' \leq 2$ and $0 < m' \leq 2$; and b) adding said solution from step a) to at least one compound (TC) of a transition metal of Group 4 to 6 and c) obtaining the solid catalyst component particles, and adding an internal electron donor (ID), preferably a non-phthalic internal donor (ID), at any step prior to step c).

The internal donor (ID) or precursor thereof is thus added preferably to the solution of step a) or to the transition metal compound before adding the solution of step a).

According to the procedure above the Ziegler-Natta catalyst (ZN-C) can be obtained via precipitation method or via emulsion-solidification method depending on the physical conditions, especially temperature used in steps b) and c). Emulsion is also called in this application liquid/liquid two-phase system.

In both methods (precipitation or emulsion-solidification) the catalyst chemistry is the same.

In precipitation method combination of the solution of step a) with at least one transition metal compound (TC) in step b) is carried out and the whole reaction mixture is kept at least at 50° C., more preferably in the temperature range of 55 to 110° C., more preferably in the range of 70 to 100° C., to secure full precipitation of the catalyst component in form of a solid particles (step c).

In emulsion—solidification method in step b) the solution of step a) is typically added to the at least one transition metal compound (TC) at a lower temperature, such as from −10 to below 50° C., preferably from −5 to 30° C. During agitation of the emulsion the temperature is typically kept at −10 to below 40° C., preferably from −5 to 30° C. Droplets of the dispersed phase of the emulsion form the active catalyst composition. Solidification (step c) of the droplets is suitably carried out by heating the emulsion to a temperature of 70 to 150° C., preferably to 80 to 110° C.

The catalyst prepared by emulsion—solidification method is preferably used in the present invention.

In a preferred embodiment in step a) the solution of $a_2$) or $a_3$) are used, i.e. a solution of (Ax') or a solution of a mixture of (Ax) and (Bx), especially the solution of $a_2$).

Preferably the Group 2 metal (MC) is magnesium.

The magnesium alkoxy compounds as defined above can be prepared in situ in the first step of the catalyst preparation process, step a), by reacting the magnesium compound with the alcohol(s) as described above, or said magnesium alkoxy compounds can be separately prepared magnesium alkoxy compounds or they can be even commercially available as ready magnesium alkoxy compounds and used as such in the catalyst preparation process of the invention.

Illustrative examples of alcohols (A) are glycol monoethers. Preferred alcohols (A) are $C_2$ to $C_4$ glycol monoethers, wherein the ether moieties comprise from 2 to 18 carbon atoms, preferably from 4 to 12 carbon atoms. Preferred examples are 2-(2-ethylhexyloxy)ethanol, 2-butyloxy ethanol, 2-hexyloxy ethanol and 1,3-propylene-glycol-monobutyl ether, 3-butoxy-2-propanol, with 2-(2-ethylhexyloxy)ethanol and 1,3-propylene-glycol-monobutyl ether, 3-butoxy-2-propanol being particularly preferred.

Illustrative monohydric alcohols (B) are of formula ROH, with R being straight-chain or branched $C_2$-$C_{16}$ alkyl residue, preferably $C_4$ to $C_{10}$, more preferably $C_6$ to $C_8$ alkyl residue. The most preferred monohydric alcohol is 2-ethyl-1-hexanol or octanol.

Preferably a mixture of Mg alkoxy compounds (Ax) and (Bx) or mixture of alcohols (A) and (B), respectively, are used and employed in a mole ratio of Bx:Ax or B:A from 10:1 to 1:10, more preferably 6:1 to 1:6, most preferably 4.1 to 1:4.

Magnesium alkoxy compound may be a reaction product of alcohol(s), as defined above, and a magnesium compound selected from dialkyl magnesium, alkyl magnesium alkoxides, magnesium dialkoxides, alkoxy magnesium halides and alkyl magnesium halides. Further, magnesium dialkoxides, magnesium diaryloxides, magnesium aryloxyhalides, magnesium aryloxides and magnesium alkyl aryloxides can be used. Alkyl groups can be a similar or different $C_1$-$C_{20}$ alkyl, preferably $C_2$-$C_{10}$ alkyl. Typical alkyl-alkoxy magnesium compounds, when used, are ethyl magnesium butoxide, butyl magnesium pentoxide, octyl magnesium butoxide and octyl magnesium octoxide. Preferably the dialkyl magnesium are used. Most preferred dialkyl magnesium are butyl octyl magnesium or butyl ethyl magnesium.

It is also possible that magnesium compound can react in addition to the alcohol (A) and alcohol (B) also with a polyhydric alcohol (C) of formula R" $(OH)_m$ to obtain said magnesium alkoxide compounds. Preferred polyhydric alcohols, if used, are alcohols, wherein R" is a straight-chain, cyclic or branched $C_2$ to $C_{10}$ hydrocarbon residue, and m is an integer of 2 to 6.

The magnesium alkoxy compounds of step a) are thus selected from the group consisting of magnesium dialkoxides, diaryloxy magnesium, alkyloxy magnesium halides, aryloxy magnesium halides, alkyl magnesium alkoxides, aryl magnesium alkoxides and alkyl magnesium aryloxides. In addition a mixture of magnesium dihalide and a magnesium dialkoxide can be used.

The solvents to be employed for the preparation of the present catalyst may be selected among aromatic and aliphatic straight chain, branched and cyclic hydrocarbons with 5 to 20 carbon atoms, more preferably 5 to 12 carbon atoms, or mixtures thereof. Suitable solvents include benzene, toluene, cumene, xylene, pentane, hexane, heptane, octane and nonane. Hexanes and pentanes are particular preferred.

The reaction for the preparation of the magnesium alkoxy compound may be carried out at a temperature of 40° to 70° C. Most suitable temperature is selected depending on the Mg compound and alcohol(s) used.

The transition metal compound of Group 4 to 6 is preferably a titanium compound, most preferably a titanium halide, like $TiCl_4$.

The internal donor (ID) used in the preparation of the catalyst used in the present invention is preferably selected from (di)esters of non-phthalic carboxylic (di)acids, 1,3-diethers, derivatives and mixtures thereof. Especially preferred donors are diesters of mono-unsaturated dicarboxylic acids, in particular esters belonging to a group comprising malonates, maleates, succinates, citraconates, glutarates, cyclohexene-1,2-dicarboxylates and benzoates, and any derivatives and/or mixtures thereof. Preferred examples are e.g. substituted maleates and citraconates, most preferably citraconates.

In emulsion method, the two phase liquid-liquid system may be formed by simple stirring and optionally adding (further) solvent(s) and additives, such as the turbulence minimizing agent (TMA) and/or the emulsifying agents and/or emulsion stabilizers, like surfactants, which are used in a manner known in the art for facilitating the formation of and/or stabilize the emulsion. Preferably, surfactants are acrylic or methacrylic polymers. Particular preferred are unbranched $C_{12}$ to $C_{20}$ (meth)acrylates such as poly(hexadecyl)-methacrylate and poly(octadecyl)-methacrylate and mixtures thereof. Turbulence minimizing agent (TMA), if used, is preferably selected from α-olefin polymers of α-olefin monomers with 6 to 20 carbon atoms, like polyoctene, polynonene, polydecene, polyundecene or polydodecene or mixtures thereof. Most preferable it is polydecene.

The solid particulate product obtained by precipitation or emulsion-solidification method may be washed at least once, preferably at least twice, most preferably at least three times with an aromatic and/or aliphatic hydrocarbons, preferably with toluene, heptane or pentane and or with $TiCl_4$. Washing solutions can also contain donors and/or compounds of Group 13, like trialkyl aluminum, halogenated alky aluminum compounds or alkoxy aluminum compounds. Aluminum compounds can also be added during the catalyst synthesis. The catalyst can further be dried, as by evaporation or flushing with nitrogen, or it can be slurried to an oily liquid without any drying step.

The finally obtained Ziegler-Natta catalyst is desirably in the form of particles having generally an average particle size range of 5 to 200 μm, preferably 10 to 100. Particles are compact with low porosity and have surface area below 20 g/m², more preferably below 10 g/m². Typically the amount of Ti is 1 to 6 wt.-%, Mg 10 to 20 wt.-% and donor 10 to 40 wt.-% of the catalyst composition.

Detailed description of preparation of catalysts is disclosed in WO 2012/007430, EP2610271, EP 2610270 and EP2610272.

The Ziegler-Natta catalyst (ZN-C) is preferably used in association with an alkyl aluminum cocatalyst and optionally external donors.

As further component in the instant polymerization process an external donor (ED) is preferably present. Suitable external donors (ED) include certain silanes, ethers, esters, amines, ketones, heterocyclic compounds and blends of these. It is especially preferred to use a silane. It is most preferred to use silanes of the general formula

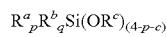

wherein $R^a$, $R^b$ and $R^c$ denote a hydrocarbon radical, in particular an alkyl or cycloalkyl group, and wherein p and q are numbers ranging from 0 to 3 with their sum p+q being equal to or less than 3. $R^a$, $R^b$ and $R^c$ can be chosen independently from one another and can be the same or different. Specific examples of such silanes are (tert-butyl)$_2$Si(OCH$_3$)$_2$, (cyclohexyl)(methyl)Si(OCH$_3$)$^2$, (phenyl)$_2$Si(OCH$_3$)$_2$ and (cyclopentyl)$_2$Si(OCH$_3$)$_2$, or of general formula

wherein $R^3$ and $R^4$ can be the same or different a represent a hydrocarbon group having 1 to 12 carbon atoms.

$R^3$ and $R^4$ are independently selected from the group consisting of linear aliphatic hydrocarbon group having 1 to 12 carbon atoms, branched aliphatic hydrocarbon group having 1 to 12 carbon atoms and cyclic aliphatic hydrocarbon group having 1 to 12 carbon atoms. It is in particular preferred that $R^3$ and $R^4$ are independently selected from the group consisting of methyl, ethyl, n-propyl, n-butyl, octyl, decanyl, iso-propyl, iso-butyl, iso-pentyl, tert.-butyl, tert.-amyl, neopentyl, cyclopentyl, cyclohexyl, methylcyclopentyl and cycloheptyl.

More preferably both $R^3$ and $R^4$ are the same, yet more preferably both $R^3$ and $R^4$ are an ethyl group.

Especially preferred external donors (ED) are the dicyclopentyl dimethoxy silane (D-donor) or the cyclohexylmethyl dimethoxy silane donor (C-Donor).

In addition to the Ziegler-Natta catalyst (ZN-C) and the optional external donor (ED) a co-catalyst can be used. The co-catalyst is preferably a compound of group 13 of the periodic table (IUPAC), e.g. organo aluminum, such as an aluminum compound, like aluminum alkyl, aluminum halide or aluminum alkyl halide compound. Accordingly, in one specific embodiment the co-catalyst (Co) is a trialkylaluminium, like triethylaluminium (TEAL), dialkyl aluminium chloride or alkyl aluminium dichloride or mixtures thereof. In one specific embodiment the co-catalyst (Co) is triethylaluminium (TEAL).

Advantageously, the triethyl aluminium (TEAL) has a hydride content, expressed as $AlH_3$, of less than 1.0 wt.-% with respect to the triethyl aluminium (TEAL). More preferably, the hydride content is less than 0.5 wt.-%, and most preferably the hydride content is less than 0.1 wt.-%.

Preferably the ratio between the co-catalyst (Co) and the external donor (ED) [Co/ED] and/or the ratio between the co-catalyst (Co) and the transition metal (TM) [Co/TM] should be carefully chosen.

Accordingly, the mol-ratio of co-catalyst (Co) to external donor (ED) [Co/ED] must be in the range of 5 to 45, preferably is in the range of 5 to 35, more preferably is in the range of 5 to 25; and optionally the mol-ratio of co-catalyst (Co) to titanium compound (TC) [Co/TC] must be in the range of above 80 to 500, preferably is in the range of 100 to 350, still more preferably is in the range of 120 to 300.

Final Articles

The unimodal polypropylene random copolymer of the present invention or the polypropylene random copolymer composition of the present invention are especially suitable for producing moulded article, like injection moulded articles, for various applications, which are intended for sterilization.

The unimodal polypropylene random copolymer of the present invention or the polypropylene random copolymer composition of the present invention are especially suitable for articles for medical or diagnostic applications intended for sterilization via gamma-radiation, such as syringes, connectors, pouches, tubes, peripheral venous catheter, butterfly winged infusion sets, protective caps or protective covers, etc.

Such moulded articles may comprise at least 50 wt.-%, like at least 70 wt.-%, more preferably at least 90.0 wt.-%, yet more preferably at least 95.0 wt.-%, still more preferably consisting of the unimodal propylene-ethylene random copolymer of the present invention or the polypropylene random copolymer composition as defined herein.

The unimodal propylene-ethylene random copolymer as well as the polypropylene random copolymer composition as defined in the instant invention may further contain up to 5.0 wt.-% additives, like phenolic or non-phenolic antioxidants, as well as slip agents, pigments and antiblocking agents.

Preferably the additive content is below 3.0 wt.-%, like below 1.0 wt.-%.

It is envisaged, that such additives may be present even if the polymer or article is defined using closed claim language (e.g. "consisting").

Further the present invention is also directed to the use of the unimodal random propylene-ethylene copolymer of the present invention or the polypropylene random copolymer composition as defined herein in the production of moulded articles, particularly injection moulded articles, The present invention is also directed to the use of the unimodal random propylene-ethylene copolymer of the present invention or the polypropylene random copolymer composition as defined herein in medical applications intended for sterilization via gamma-radiation, such as syringes, connectors, pouches, tubes, peripheral venous catheter, butterfly winged infusion sets, protective caps or protective covers, etc.).

The present invention will now be described in further detail by the examples provided below:

EXAMPLES

Measuring Methods
Irradiation

Injection moulded test specimen of 80×10×4 mm$^3$ prepared in accordance with EN ISO 1873-2 were exposed to gamma irradiation at 25 and 50 kGy using a $^{60}$Co γ-ray source.

Consecutively the samples were aged at 80° C. in a circulating air oven up to 150 days as indicated below.

Once the desired time was reached, the samples were taken out from the oven and aged at 23° C. for 24 hours before the impact test according to Charpy ISO 179/1eA+ 23° C. was performed.

Description of Quantitative $^{13}$C NMR Spectroscopy

Quantitative nuclear-magnetic resonance (NMR) spectroscopy was used to quantify the comonomer content of the polymers, comonomer dyad sequence distribution and sequence order parameter quantification.

Quantitative $^{13}$C{$^1$H} NMR spectra were recorded in the solution-state using a Bruker Avance III 400 NMR spectrometer operating at 400.15 and 100.62 MHz for $^1$H and $^{13}$C respectively. All spectra were recorded using a $^{13}$C optimised 10 mm extended temperature probehead at 125° C. using nitrogen gas for all pneumatics. Approximately 200 mg of material was dissolved in 3 ml of 1,2-tetrachloroethane-d$_2$ (TCE-d$_2$) along with chromium-(III)-acetylacetonate (Cr(acac)$_3$) resulting in a 65 mM solution of relaxation agent in solvent (Singh, G., Kothari, A., Gupta, V., Polymer Testing 28 5 (2009), 475). To ensure a homogenous solution, after initial sample preparation in a heat block, the NMR tube was further heated in a rotatory oven for at least 1 hour. Upon insertion into the magnet the tube was spun at 10 Hz. This setup was chosen primarily for the high resolution and quantitatively needed for accurate ethylene content quantification. Standard single-pulse excitation was employed without NOE, using an optimised tip angle, 1 s recycle delay and a bi-level WALTZ16 decoupling scheme (Zhou, Z., Kuemmerle, R., Qiu, X., Redwine, D., Cong, R., Taha, A., Baugh, D. Winniford, B., J. Mag. Reson. 187 (2007) 225; Busico, V., Carbonniere, P., Cipullo, R., Pellecchia, R., Severn, J., Talarico, G., Macromol. Rapid Commun. 2007, 28, 1128). A total of 6144 (6 k) transients were acquired per spectra.

Comonomer Content Quantification of Poly(Propylene-Co-Ethylene) Copolymers

Quantitative $^{13}$C{$^1$H} NMR spectra were processed, integrated and relevant quantitative properties determined from the integrals using proprietary computer programs. All chemical shifts were indirectly referenced to the central methylene group of the ethylene block (EEE) at 30.00 ppm using the chemical shift of the solvent. This approach allowed comparable referencing even when this structural unit was not present. Characteristic signals corresponding to the incorporation of ethylene were observed (Cheng, H. N., Macromolecules 17 (1984), 1950) and the comonomer fractions calculated as the fraction of ethylene and propylene in the polymer with respect to all monomer in the polymer:

$$fE=E/(P+E)$$

$$fP=P/(P+E)$$

The comonomer fraction was quantified using the method of Wang et. al. (Wang, W.-J., Zhu, S., Macromolecules 33 (2000), 1157) through integration of multiple signals across the whole spectral region in the $^{13}$C{$^1$H} spectra.

The mole percent comonomer incorporation was calculated from the mole fraction:

$$E[\text{mol \%}]=100*fE$$

The weight percent comonomer incorporation was calculated from the mole fraction:

$$E[\text{wt.-\%}]=100*(fE*28.06)/((fE*28.06)+((1-fE)*42.08))$$

Comonomer Dyad Sequences Determination

Comonomer sequence distribution was quantified at the dyad level using the characteristic signals corresponding to the incorporation of ethylene into propylene-ethylene copolymers (Cheng, H. N., Macromolecules 17 (1984), 1950). Integrals of respective sites were taken individually, the regions of integration described in the article of Wang et. al. were not applied for dyad sequence quantification.

It should be noted that due to overlapping of the signals of Tβδ and Sγγ, the compensation equations were applied for integration range of these signals using the sites Sβδ and Sγδ:

$S\gamma\gamma=(I(S\beta\delta)-I(S\gamma\delta))/2$ $T\beta\delta=I(T\beta\delta+S\gamma\gamma)-(I(S\beta\delta)-I(S\gamma\delta))/2$ The constitutive equations were:

$EP=2*T\delta\delta+T\beta\delta=2*I(T\delta\delta)+I(T\beta\delta+S\gamma\gamma)-(I(S\beta\delta)-I(S\gamma\delta))/2$ $EE=S\gamma\gamma+S\gamma\delta+(S\delta\delta-S\gamma\delta/2)/2=0.5*I(S\beta\delta)+0.5*I(S\delta\delta)+0.25*I(S\gamma\delta)$ $PP=T\beta\delta/2+T\beta\beta=0.5*(I(T\beta\delta+S\gamma\gamma)-(I(S\beta\delta)-I(S\gamma\delta))/2)+I(T\beta\beta)$ Note that for simplicity the two indistinguishable reversible PE and EP dyads are termed EP i.e. EP=PE+EP. The mole fraction of each dyad was determined through normalisation to the sum of all dyads.

$XX=PP+EP+EE$ $fPP=PP/XX$ $fEP=EP/XX$ $fEE=EE/XX$

Sequence Order Parameter Description and Quantification

Sequence order parameter, $\chi$ as it is defined by Koenig (Spectroscopy of Polymers, Lack. L Koenig. American Chemical Society, Washington, D.C. 1992) (or "Koenig B-value" as it is named in WO 2010/078479 A1), yields information about whether the distribution of the structures is random, i.e. can be described by Bernoullian statistics, and whether it tends towards an alternating or block distribution. This parameter can be determined by the formula:

$B_{Koenig}=fEP/(2*fE*fP)$

Cross Fractionation Chromatography CFC (a-TREF× SEC)

The chemical composition distribution as well as the determination of the molecular weight distribution and the corresponded molecular weight averages (Mn, Mw and Mv) at a certain elution temperature (polymer crystallinity in solution) were determined by a full automated Cross Fractionation Chromatography (CFC) as described by Ortin A., Monrabal B., Sancho-Tello J., Macromol. Symp., 2007, 257, 13-28.

A CFC instrument (PolymerChar, Valencia, Spain) was used to perform the cross-fractionation chromatography (TREF×SEC). A four band IRS infrared detector (PolymerChar, Valencia, Spain) was used to monitor the concentration. Around 40 mg of the polymer sample was dissolved in 25 ml TCB in the stainless steel vessel for 150 min at 150° C. Once the sample was completely dissolved an aliquot of 0.5 ml was loaded into the TREF column and stabilized for a while at 110° C. The polymer was crystallized and precipitate to a temperature of 30° C. by applying a constant cooling rate of 0.1° C./min. A discontinuous elution process is performed using the following temperature steps: (30, 40, 50, 60, 70, 75, 80, 84, 88, 92, 95, 98, 100, 102, 104, 106, 108, 110, 115, 120, 130 and 140).

In the second dimension, the GPC analysis, 3 PL Olexis columns and 1× Olexis Guard columns from Agilent (Church Stretton, UK) were used as stationary phase. As eluent 1,2,4-trichlorobenzene (TCB, stabilized with 250 mg/L 2,6-Di tert butyl-4-methyl-phenol) at 150° C. and a constant flow rate of 1 mL/min were applied. The column set was calibrated using universal calibration (according to ISO 16014-2:2003) with at least 15 narrow MWD polystyrene (PS) standards in the range of 0.5 kg/mol to 11 500 kg/mol. Following Mark Houwink constants were used to convert PS molecular weights into the PP molecular weight equivalents.

$K_{PS}=19\times 10^{-3}$ mL/g, $\alpha_{PS}=0.655$ $K_{PP}=19\times 10^{-3}$ mL/g, $\alpha_{PP}=0.725$ A third order polynomial fit was used to fit the calibration data. Data processing was performed using the software provided from PolymerChar with the CFC instrument.

Comonomer Distribution (CD)

Comonomer distribution (CD) is determined based on the CFC contour plot and the extracted a-TREF from the corresponding CFC analysis.

Determination of $T_{80}$-$T_{20}$ (PP)

The broadness of the comonomer distribution can be estimated from the $T_{80}$-$T_{20}$(PP) value. This can be determined by calculating the temperature difference between two specific elution temperatures in the TREF profile obtained by CFC analysis:

$T_{80}$ (elution temperature, at which 80% of the polymer is eluting)

$T_{20}$ (elution temperature, at which 20% of the polymer is eluting)

Broadness of Peak at 25% of the Peak Height

The broadness of elution peak at 25% of the peak height can be determined in the following way:

1. Determine the elution peak with the highest peak in the TREF fractogram
2. Calculate the peak width at quarter height in ° C. ($W_{1/4}$)

Melt Flow Rate

The melt flow rate (MFR) is determined according to ISO 1133 and is indicated in g/10 min. The MFR is an indication of the flowability, and hence the processability, of the polymer. The higher the melt flow rate, the lower the viscosity of the polymer. The $MFR_2$ of polypropylene is determined at a temperature of 230° C. and a load of 2.16 kg.

Xylene Cold Soluble

Xylene Cold Soluble fraction at room temperature (XCS, wt.-%) is determined at 25° C. according to ISO 16152; $5^{th}$ edition; 2005 Jul. 1.

Flexural Modulus

The flexural modulus was determined in 3-point-bending at 23° C. according to ISO 178 on 80×10×4 mm³ test bars injection moulded in line with EN ISO 1873-2.

Notched Impact Strength (NIS+23):

The Charpy notched impact strength (NIS+23) was measured according to ISO 179 1eA at +23° C., using injection moulded bar test specimens of 80×10×4 mm³ prepared in accordance with EN ISO 1873-2.

$\gamma NIS_{(rad;\ days)}$ denominates Notched impact strength (NIS+23) determined after irradiation and heat exposure at 80° C., wherein "rad" denominates the irradiation (50 kGy) and "days" denominates the duration of heat exposure at 80° C. in circulating air of the irradiated sample in days.

Accordingly $NIS_{(0;\ days)}$ denominates the notched impact strength determined samples that underwent heat exposure at 80° C. for the given days in circulating air without preceding irradiation.

Retained

Notched Impact Strength after Radiation $rNIS_{(rad;\ days)}$ is determined by putting into relation the notched impact strength of an irradiated and heat aged sample ($\gamma NIS_{(rad;\ days)}$) to the $NIS_{(0;\ days)}$ of the same, heat-aged but non-irradiated material:

$$rNIS_{(rad;days)}[\%] = \frac{\gamma NIS_{(rad;days)} * 100}{NIS_{(0;days)}} \qquad \text{(Equ. I)}$$

Based on the values given below, the retained Impact Strength after Radiation $rNIS_{(50,60)}$ for IE1 after 50 kGy and 60 days would be:

4.6/5.1*100=90.2%

Phthalic Acid Esters and Decomposition Products

Detection is carried out by gas chromatography coupled with one- or two-dimensional mass spectrometry (GC-MS respectively GC-MS/MS) optionally preceded by enrichment on a suitable adsorption material.

"Free of phthalic acid esters as well as decomposition products thereof" indicates a maximum of 10 μg/kg, i.e. 10 ppb by weight.

Typical equipment to be used is for example given in H. Fromme, T. Kuchler, T. Otto, K. Pilz, J. Müller, A. Wenzel Water Research 36 (2002) 1429-1438.

Material Description:

All the polymers were stabilised with 1500 ppm Tinuvin 622, 1000 ppm Irgafos 168 (both supplied by BASF and others), 500 ppm Calcium-stearat, 2000 ppm Millad 3988 (supplied by Milliken) and 2 wt.-% CA8200 (LDPE, supplied by Borealis).

The person skilled in the art is aware that phenolic antioxidants tend to discolorate during irradiation; therefor stabilisation systems which are free of phenolic antioxidants are to be preferred.

Catalyst Description: For IE1:

Preparation of a Mg Complex

First a magnesium alkoxide solution was prepared by adding, with stirring (70 rpm), into 1 l kg of a 20 wt-% solution in toluene of butyl ethyl magnesium (Mg(Bu)(Et), BEM), a mixture of 4.7 kg of 2-ethylhexanol and 1.2 kg of butoxypropanol in a 20 l stainless steel reactor. During the addition the reactor contents were maintained below 45° C. After addition was completed, mixing (70 rpm) of the reaction mixture was continued at 60° C. for 30 minutes.

After cooling to room temperature 2.3 kg g of the donor bis(2-ethylhexyl)citraconate was added to the Mg-alkoxide solution keeping temperature below 25° C. Mixing was continued for 15 minutes under stirring (70 rpm)

Preparation of Solid Catalyst Component 20.3 kg of $TiCl_4$ and 1.1 kg of toluene were added into a 20 l stainless steel reactor. Under 350 rpm mixing and keeping the temperature at 0° C., 14.5 kg of the Mg complex prepared in example 1 was added during 1.5 hours. 1.7 l of Viscoplex® 1-254 and 7.5 kg of heptane were added and after 1 hour mixing at 0° C. the temperature of the formed emulsion was raised to 90° C. within 1 hour. After 30 minutes mixing was stopped catalyst droplets were solidified and the formed catalyst particles were allowed to settle. After settling (1 hour), the supernatant liquid was siphoned away.

Then the catalyst particles were washed with 45 kg of toluene at 90° C. for 20 minutes followed by two heptane washes (30 kg, 15 min). During the first heptane wash the temperature was decreased to 50° C. and during the second wash to room temperature.

The solid catalyst component was used along with triethyl-aluminium (TEAL) as co-catalyst and cyclohexylmethyl dimethoxy silane (C-donor) as donor.

Catalyst Description for CE1

The catalyst used in the polymerization processes of the comparative example (CE1) was prepared as described now:

First, 0.1 mol of $MgCl_2 \times 3$ EtOH was suspended under inert conditions in 250 ml of decane in a reactor at atmospheric pressure. The solution was cooled to the temperature of −15° C. and 300 ml of cold $TiCl_4$ was added while maintaining the temperature at said level. Then, the temperature of the slurry was increased slowly to 20° C. At this temperature, 0.02 mol of dioctylphthalate (DOP) was added to the slurry. After the addition of the phthalate, the temperature was raised to 135° C. during 90 minutes and the slurry was allowed to stand for 60 minutes. Then, another 300 ml of $TiCl_4$ was added and the temperature was kept at 135° C. for 120 minutes. After this, the catalyst was filtered from the liquid and washed six times with 300 ml heptane at 80° C. Then, the solid catalyst component was filtered and dried.

Catalyst and its preparation concept is described in general e.g. in patent publications EP491566, EP591224 and EP586390.

The catalyst was used along with triethyl-aluminium (TEAL) as co-catalyst and cyclohexylmethyl dimethoxy silane (C-donor) as donor.

Polymerization

The polymerization was done in a Borstar pilot plant with a prepolymerization reactor and a loop reactor for IE1 and CE1. The polymerization conditions are indicated in table 1.

TABLE 1

| Polymerization Data: | | | |
|---|---|---|---|
| | | IE1 | CE1 |
| Prepolymerization | | | |
| Temperature | [° C.] | 30 | 30 |
| TEAL | [g/t C3] | 170 | 170 |
| Donor | [g/t C3] | 40 | 40 |
| Donor type | | C | C |
| Reisdence time | [min] | 20 | 20 |
| Loop | | | |
| Temperature | [° C.] | 70 | 70 |
| Pressure | [bar] | 55 | 55 |
| Residence time | [min] | 30 | 30 |
| H2/C2 | [mol/kmol] | 4.3 | 5.6 |
| C2/C3 | [mol/kmol] | 8.0 | 8.0 |

Polymer Results

TABLE 2

| Polymer - Basic features | | | |
|---|---|---|---|
| | | IE1 | CE1 |
| MFR | [g/10 min] | 20 | 20 |
| C2 total | [wt.-%] | 3.85 | 3.51 |
| XCS | [wt.-%] | 5.5 | 6.5 |
| Flexural Modulus | [MPa] | 980 | 1100 |
| Charpy NIS + 23° C. | [kJ/m$^2$] | 5.8 | 5.5 |
| NMR: | | | |
| EE | [mol %] | 1.16 | 1.14 |
| EP/PE | [mol %] | 8.51 | 8.37 |
| PP | [mol %] | 90.35 | 90.50 |

TABLE 2-continued

| Polymer - Basic features | | | |
|---|---|---|---|
| | | IE1 | CE1 |
| E | [mol %] | 5.67 | 5.18 |
| P | [mol %] | 94.33 | 94.82 |
| Koenig B = [EP/PE]/(2*[E]*[P]) | [—] | 0.82 | 0.88 |
| CFC | | | |
| Comonomer Distribution (25% peak height) | [—] | 12.5 | 16.2 |
| T80-T20 | [—] | 19.9 | 24.8 |

The diagram shown in FIG. 1 indicates the CFC contour plot and the extracted a-TREF curve as well as an indication on the respective value for comonomer distribution (CD).

TABLE 3

Impact Strength (NIS 23° C. [kJ/m$^2$]) after Irradiation with 25 kGy and Heat Exposure at 80° C.:

| | NIS + 23° C. [kJ/m$^2$] | | | |
|---|---|---|---|---|
| | IE 1 | | CE1 | |
| Days @80° C. | 0 kGy | 25 kGy | 0 Kgy | 25 kGy |
| 3 | 5.8 | 5.6 | 5.6 | 5.1 |
| 4 | 5.8 | 5.3 | 5.4 | 4.5 |
| 7 | 5.7 | 5.6 | 5.6 | 5.2 |
| 14 | 5.6 | 5.3 | 5.5 | 4.9 |
| 30 | 5.8 | 5.3 | 5.6 | 5.2 |
| 60 | 5.1 | 4.5 | 4.5 | 3.7 |
| 90 | 5.7 | 5.5 | 5.3 | 4.9 |
| 120 | 6.1 | 5.7 | 5.6 | 4.8 |
| 150 | 5.1 | 5.2 | 4.7 | 4.6 |

TABLE 4

Impact Strength (NIS 23° C. [kJ/m$^2$]) after Irradiation with 50 kGy and Heat Exposure at 80° C.:

| | NIS + 23° C. [kJ/m$^2$] | | | |
|---|---|---|---|---|
| | IE 1 | | CE1 | |
| Days @80° C. | 0 Kgy | 50 kGy | 0 Kgy | 50 kGy |
| 3 | 5.8 | 5.7 | 5.6 | 4.8 |
| 4 | 5.8 | 4.8 | 5.4 | 4.6 |
| 7 | 5.7 | 5.3 | 5.6 | 5.2 |
| 14 | 5.6 | 5.4 | 5.5 | 4.6 |
| 30 | 5.8 | 5.6 | 5.6 | 4.6 |
| 60 | 5.1 | 4.6 | 4.5 | 3.3 |
| 90 | 5.7 | 4.9 | 5.3 | 3.9 |
| 120 | 6.1 | 5.4 | 5.6 | 4.3 |
| 150 | 5.1 | 5.2 | 4.7 | 3.8 |

TABLE 5

Retained Impact strength (rNIS$_{(50; days)}$) [%] after Radiation with 50 kGy and Heat treatment

| | [%] | |
|---|---|---|
| Days @ 80° C. | IE1 | CE1 |
| 60 | 90.2 | 73.9 |
| 90 | 86.0 | 73.8 |
| 120 | 89.3 | 75.8 |
| 150 | 102.4 | 80.0 |

The invention claimed is:

1. A unimodal polypropylene random copolymer of propylene and 2.0-4.5 wt.-% of ethylene as comonomer characterised by a comonomer distribution (CD) determined via a-TREF of at most 16.0[–] and being polymerized in the presence of a Ziegler-Natta catalyst, wherein the unimodal polypropylene random copolymer has a Melt Flow Rate determined according to ISO1133 at 230° C. and 2.16 kg (MFR230/2.16) of 10.0 to 25.0 g/10 min.

2. The unimodal polypropylene random copolymer according to claim 1 further characterised by a randomness (Koenig B) of at least 0.8 [–].

3. The unimodal polypropylene random copolymer according to claim 1, having a Melt Flow Rate determined according to ISO1133 at 230° C. and 2.16 kg (MFR230/2.16) of 15.0 to 22.0 g/10 min.

4. The unimodal polypropylene random copolymer according to claim 1, being free of phthalic acid esters as well as their respective decomposition products.

5. The unimodal polypropylene random copolymer according to claim 1 being polymerized in the presence of a Ziegler-Natta catalyst, wherein the Ziegler Natta catalyst comprises
   a) at least one compound of a transition metal of Group 4 to 6 of IUPAC,
   b) a Group 2 metal compound,
   c) an internal donor, wherein said internal donor is a non-phthalic compound,
   d) optionally a co-catalyst, and
   e) optionally an external donor.

6. The unimodal polypropylene random copolymer according to claim 5, wherein the internal donor is selected from (di)esters of non-phthalic carboxylic (di)acids, 1,3-diethers, derivatives and mixtures thereof.

7. A moulded article comprising the unimodal propylene-ethylene random copolymer according to claim 1.

8. The moulded article according to claim 7 wherein the moulded article is a medical, pharmaceutical or diagnostic article.

9. A method comprising sterilizing the moulded article according to claim 8 via gamma-irradiation.

10. A polypropylene random copolymer composition comprising a unimodal polypropylene random copolymer of propylene and 2.0-4.5 wt.-% of ethylene as comonomer, wherein the unimodal polypropylene random copolymer comprised by said polypropylene random copolymer composition is characterised by a comonomer distribution (CD) determined via a-TREF of at most 16.0 [–] and has a Melt Flow Rate determined according to ISO1133 at 230° C. and 2.16 kg (MFR230/2.16) of 10.0 to 25.0 g/10 min.

11. The polypropylene random copolymer composition according to claim 10, wherein the unimodal polypropylene random copolymer comprised by said polypropylene random copolymer composition is characterised by a randomness (Koenig B) of at least 0.8 [–].

12. The polypropylene random copolymer composition according to claim 10, characterised by a retained notched Impact Strength rNIS after irradiation with 50 kGy (rNIS (50; days)) according the formula $$rNIS_{(50;days)}[\%] = \frac{\gamma NIS_{(50;days)} * 100}{NIS_{(0;days)}}$$

of at least 85.0%, wherein "days" is heat exposure at 80° C. for at least 60 days.

13. The polypropylene random copolymer composition according to claim 10, comprising at least 50 wt.-% of the unimodal polypropylene random copolymer.

14. The polypropylene random copolymer composition according to claim 10, wherein the polypropylene random copolymer composition has a Melt Flow Rate determined according to ISO1133 at 230° C. and 2.16 kg (MFR230/2.16) of 15.0-22.0 g/10 min.

15. The polypropylene random copolymer composition according to claim 12, wherein "days" is heat exposure at 80° C. for at least 90 days.

16. A moulded article comprising the polypropylene random copolymer composition according to claim 10.

17. The moulded article according to claim 16, wherein the moulded article is medical, pharmaceutical or diagnostic article.

18. A method comprising sterilizing the moulded article according to claim 17 via gamma-irradiation.

* * * * *